United States Patent [19]

Bourrié et al.

[11] Patent Number: 4,597,220
[45] Date of Patent: Jul. 1, 1986

[54] CLOSED ENCLOSURE USED AS GREENHOUSE, CULTIVATION FRAME OR FISH POND AND IMPROVING EXPLOITATION CONDITIONS

[75] Inventors: Andre R. J. Bourrié, Mantes La Jolie; Jacques L. R. Maroselli, Luxeuil Les Bains, both of France

[73] Assignees: Andre Bourrie; Jacques Maroselli, both of Mantes La Jolie, France

[21] Appl. No.: 591,794

[22] Filed: Mar. 21, 1984

[30] Foreign Application Priority Data

Mar. 22, 1983 [FR] France ............................... 83 04648

[51] Int. Cl.⁴ ................................................ A01G 9/24
[52] U.S. Cl. .......................................... 47/27; 47/69; 47/28 R
[58] Field of Search ............................... 47/27-31, 47/17, 19, 65, 69, 16, 84, 71, 61, 81; 251/353

[56] References Cited

U.S. PATENT DOCUMENTS

| | | | |
|---|---|---|---|
| 135,173 | 1/1873 | Timby | 47/30 |
| 327,510 | 10/1885 | Anderson | 47/28 |
| 757,045 | 4/1904 | Lane | 47/28 |
| 992,529 | 5/1911 | Abraham | 47/19 |
| 1,621,440 | 3/1927 | Stoddard | 47/19 |
| 2,011,897 | 8/1935 | Hanck | 47/29 |
| 2,626,483 | 1/1953 | Service | 47/29 X |
| 3,106,801 | 10/1963 | Risacher | 47/19 |
| 3,794,294 | 2/1974 | Sherman | 251/353 X |
| 3,939,607 | 2/1976 | Spector | 47/69 |
| 4,160,340 | 7/1979 | Levett | 47/28 X |
| 4,222,196 | 9/1980 | Pointon | 47/29 X |
| 4,285,162 | 8/1981 | Hilton | 47/29 |
| 4,369,598 | 1/1983 | Beckwith | 47/81 X |
| 4,392,326 | 7/1983 | Boria | 47/28 |
| 4,406,072 | 9/1983 | van Iterson | 47/29 X |

FOREIGN PATENT DOCUMENTS

| | | | |
|---|---|---|---|
| 2714059 | 10/1978 | Fed. Rep. of Germany | 47/28 |
| 2363981 | 5/1978 | France | 47/27 |
| 2376617 | 9/1978 | France | 47/29 |
| 729869 | 12/1966 | Italy | 47/29 |
| 698744 | 10/1953 | United Kingdom | 47/29 |

Primary Examiner—Robert A. Hafer
Assistant Examiner—Danton DeMiller
Attorney, Agent, or Firm—Browdy and Neimark

[57] ABSTRACT

A closed enclosure used as greenhouse, cultivation frame or fish pond and improving exploitation conditions, in which a structure covers totally living organisms to be protected or breeded either directly in the ground or in a culture medium placed in a box. At least one removable cover has edges defining at least one central recessed portion through which extends a multitude of holes or slits having dimensions calculated so as to provide a convenient watering in quantity and quality of liquid contained in the recessed portion towards the culture medium.

13 Claims, 16 Drawing Figures

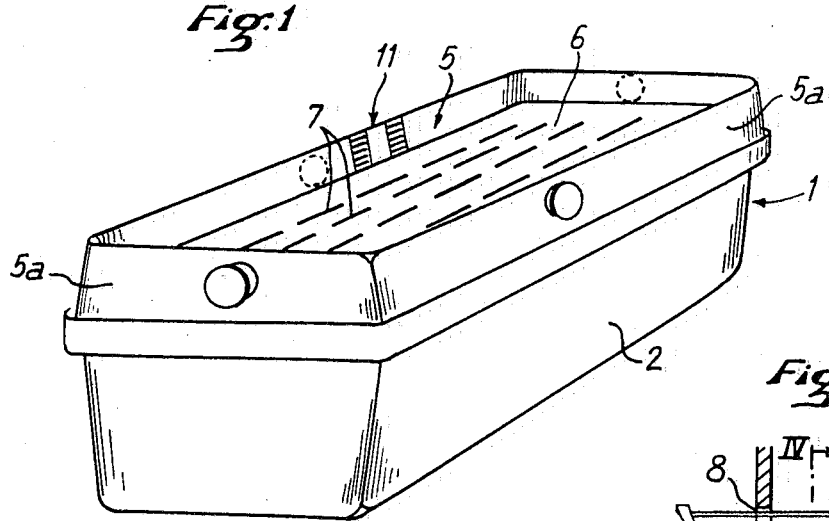
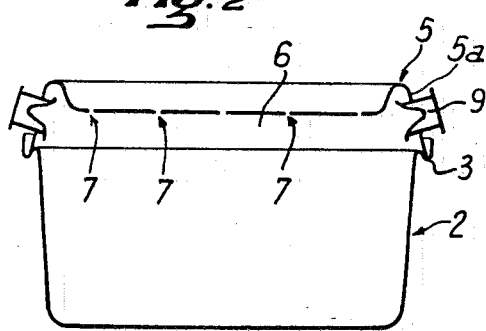
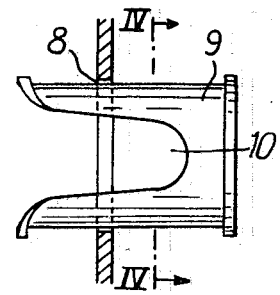
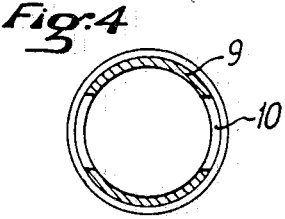
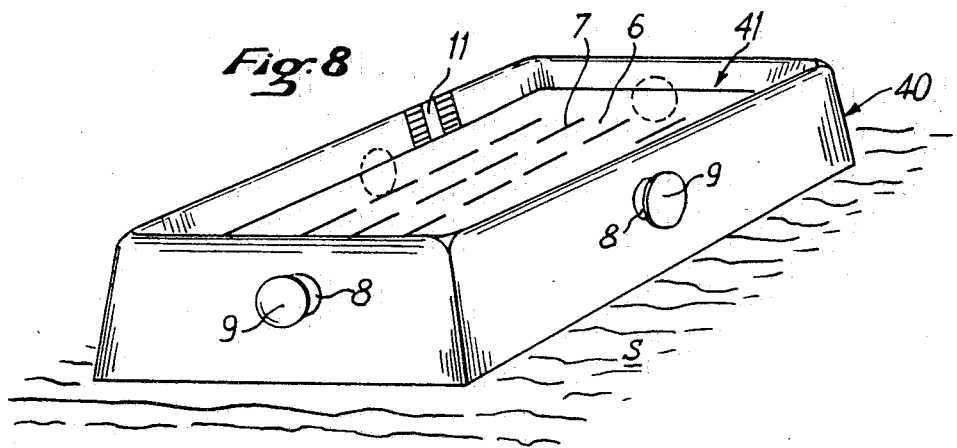

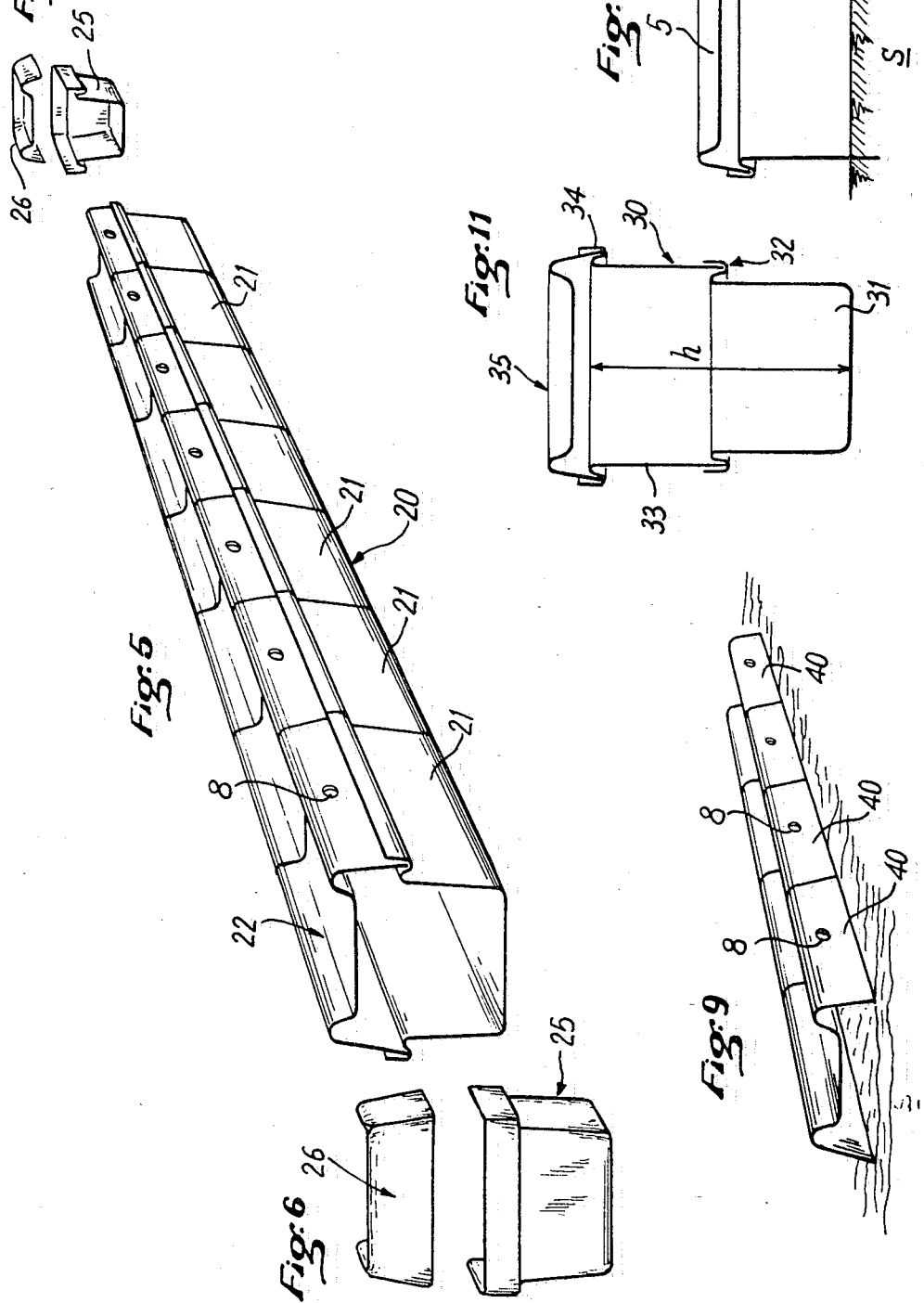

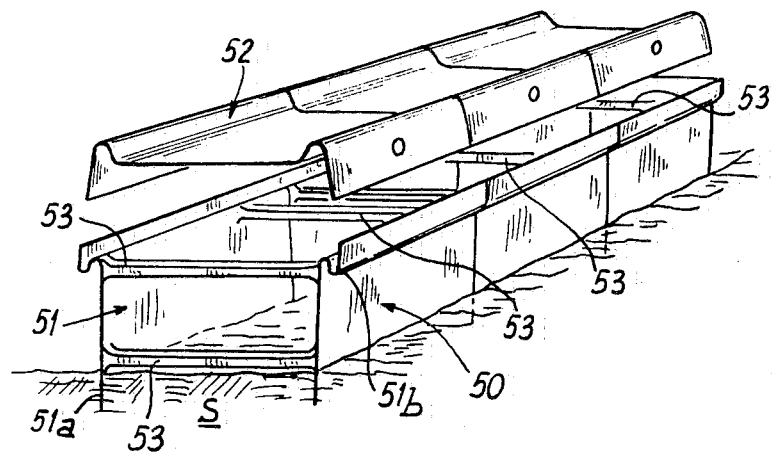
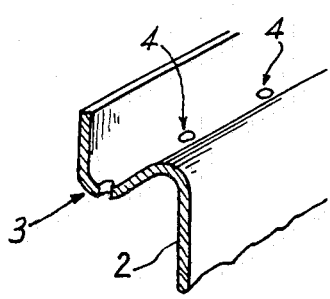
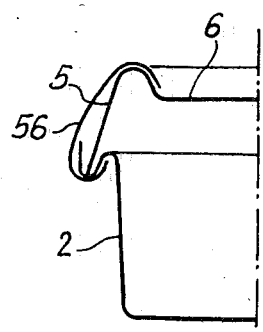
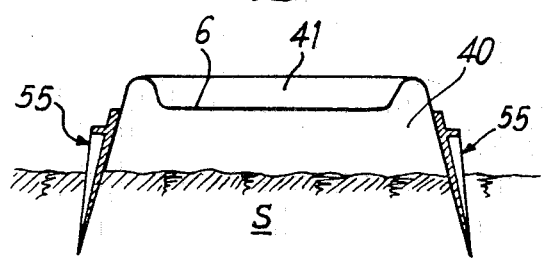
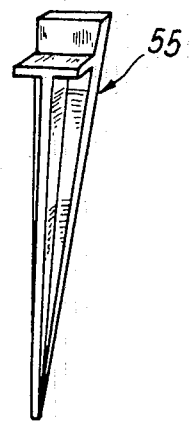

CLOSED ENCLOSURE USED AS GREENHOUSE, CULTIVATION FRAME OR FISH POND AND IMPROVING EXPLOITATION CONDITIONS

BACKGROUND OF THE INVENTION

Enclosures for the intensive production of plants, particularly from seeds, these enclosures being called: frames, small glasshouses, transparent or translucent glass or plastics greenhouse are already known and widely used for cultivations of plant seedlings, flowers or similar. Such enclosures provide a protection of the vegetables against frost since the enclosures maintain a tepid and moist ambience favourable for the vegetable germination, growth or cultivation, and even for the breeding of small animals. However such enclosures, although they have given rather good results, require a lengthy and delicate work which has to be carried out right in time. Moreover, such enclosures withstand badly brutal spells of bad weather such as storms, heavy snow falls or hard frosts. Moreover, it is necessary on the one hand to provide various complicated and costly means for a periodical watering highly supervised in quality and quantity, and on the other hand to sometimes complete by a heat supply the temperature prevailing inside such enclosures.

The present invention remedies these disadvantages by providing closed enclosures the upper portion or cover of which has a shape such that there is provided a very simple setting of its operation, thereby greatly reducing the work to be done and the maintenance costs.

SUMMARY OF THE INVENTION

According to the invention, the enclosure is made of at least one removable cover having edges defining at least one central recessed portion through which extends a multitude of holes or slits having dimensions calculated so as to ensure a convenient watering, as regards both quantity and quality of the liquid contained in the recessed portion, towards the culture medium; upper side walls of the enclosure are formed with holes which are normally closed by plugs of corresponding shape, the plugs having at least one radial slot for setting a quantity of air admitted under the closed enclosure; and inner walls of the enclosure defining the recessed portion comprise a graduated scale for measuring a quantity of watering liquid.

According to a further feature of the invention, lower boxes are bordered at their upper portion by edges through which extend holes promoting a removal of excess watering liquid, the edges providing a connection between a protection enclosure and the box.

Various other features of the invention will become more apparent from the following detailed description.

BRIEF DESCRIPTION OF THE DRAWINGS

Embodiments of the invention are shown by way of non limiting examples in the accompanying drawings, wherein:

FIG. 1 is a perspective view of a first embodiment of the invention;

FIG. 2 is a cross sectional view of the enclosure of FIG. 1;

FIG. 3 is a partial enlarged cross sectional view showing a detail of FIG. 1;

FIG. 4 is a cross sectional view along line IV—IV of FIG. 3;

FIG. 5 is a perspective view of an alternative embodiment of the enclosure of FIG. 1;

FIGS. 6 and 7 are perspective views of the ends of the enclosure of FIG. 5;

FIG. 8 is a perspective view of an other embodiment of the enclosure;

FIG. 9 is a perspective view of a variant of FIG. 8;

FIG. 10 is a sectional view of an other variant of FIG. 6;

FIG. 11 is a sectional view of another possible variant of FIG. 5;

FIG. 12 is a perspective view of a variant of FIG. 10;

FIGS. 13, 14 and 15 are perspective and elevation cross sectional views of sligh alternatives or details usuable in the variants of FIGS. 9, 10 and 11;

FIG. 15a is a front elevation view of a support member.

DETAILED DESCRIPTION OF THE INVENTION

In FIG. 1 is shown an enclosure 1 made of a lower tank or box 2 having substantially the shape of a rectangular parallelepipedon the upper edge 3 of which surrounding the box 2 on its four sides having in cross-section the shape of letter "S" (see FIG. 13). Holes 4 are generally formed into the bottom of the "S" so as to remove the excess water or liquid possibly falling from the edges of cover 5 (see FIGS. 2 and 3), the cover 5 having in its center a recessed portion 6 through which extends a multitude of holes or slits 7 allowing watering of the plants cultivated inside the box 2 with water or a mixture of water and fertilizers or others. The openings 7 have sizes in relation with the surface to be cultivated and defined by the surface of the box 2.

Moreover and as shown in FIGS. 1 and 1, the cover 5 is formed, on its side walls 5a, with holes 8 which are normally closed by plugs 9 of cylindrical shape but comprising at least a radial slot 10 for allowing a greater or lesser quantity of air inside the enclosure 1. By completely driving-in the plugs 9 into the holes 8, it is also possible to completely close the latter, particularly during periods where frost can damage the plants cultivated inside the enclosure 1. The recessed portion 6 of the cover 5 has, on one of its faces, a graduated scale 11 (see FIG. 1) for measuring the quantity of liquid placed in the cover 5. Thus, inside the enclosure can prevail a temperature controllable by means of known instruments, but also sufficient watering of the plants developing therein. This watering, due to the slowness of water penetration inside the enclosure 1 through the openings 7, enables postponing this operation which therefore can be carried out easily and is no more a demanding obligation.

The hereabove described enclosure is particularly adapted to cultivations in small quantities, for example personal cultivations of flowers. But when it is required to carry out cultivations in a larger size, it is necessary to use much larger enclosures, of the type of those shown in FIG. 5. In such a case, these enclosures 20 include a lower box 21 the ends of which are free and opened so as to offer the possibility of flanking several boxes 21 side by side as shown in FIG. 5. Covers 22 are also provided without side panels and the covers can therefore be placed side by side for forming a desired length of box comprising all the devices hereabove described with reference to FIG. 1. Finally, the enclosure 20 can be closed at its ends by lower 25 and upper 26 end-pieces, as shown in FIGS. 6 and 7. Thus, it is possible to obtain an enclosure of a considerable volume allowing a large number of cultivations. In some cases where the plants are provided to be of a great height, the enclosures 30 (see FIG. 11) are formed of a lower box 31 with S-shaped edges 32 on which is placed a cage 33 having S-shaped edges 34 covered by a cover 35 of the type as hereabove described. The heigh h therefore allows cultivating plants of a great height.

When it is required to carry out cultivations on the ground S itself, the lower boxes are not necessary, and there is then used enclosures 40 (see FIGS. 8, 9) formed exclusively of a cover 41 identical to the hereabove described cover; thus, the plants can be directly cultivated in the ground while protecting them by a tunnel formed of one or several enclosures 40 without having to do a lengthy, laborious and arduous work.

In FIG. 9 are shown covers 40 which do not include transverse elements so as to flank them side by side, these covers 40 being usable with end-pieces not shown but of the type of those described, such as the upper end-pieces 26 (see FIGS. 6 and 7).

FIG. 10 shows a variant of FIG. 9 in which a bottomless enclosure 100 is placed directly on the ground S and the lower edges 101 of which extend into the ground. The upper edges 102 are as hereabove described (see FIG. 2) and support a cover 5 identical to those previously described. Thus, plants of a certain height can be cultivated in the enclosure thus formed.

In FIG. 12, the enclosure 50 is provided for allowing cultivation on the ground of plants protected by casings 51 of a substantially rectangular parallelepipedal shape, the lower edge 51a of which is driven into the ground S and the upper edge 51b of which is S-shaped, as hereabove described, with the possibility of including perforations, as the holes 4 (see FIG. 13). Covers 52 are identical to those hereabove described and, particularly, to those described with reference to FIG. 9. In order to strengthen transversely the casings 51, they include crossbeams 53 from distance to distance. Of course, the enclosure 50 forming a tunnel can also comprise at its ends end-pieces as those described with reference to FIG. 6, viz. bottomless end-pieces and upper end-pieces identical to those described under reference 26.

In the case where the enclosures described with reference to FIGS. 8 and 9 are used, it is possible to maintain the enclosures in the ground S (see FIG. 15) by means of pegs 55 (FIG. 15a) which, by penetrating into the ground S, encompass reliably the side walls of enclosures 40, thereby avoiding any displacement of these enclosures under action of wind. The pegs 55 act as specific support in the opened position of the enclosures, which have the advantage of being openable on either side.

Finally and as shown in FIG. 14, in the case of enclosures 1, 20, 30, 100, it is possible to lock the cover 5 onto the boxes 2 by resilient fasteners 56, thereby maintaining the covers 5 closed onto the boxes 2. There is thus provided a security against wind.

The hereabove described enclosures can be made of any material but they are generally made of antirot rigid transparent or translucent plastics material.

The hereabove description shows that a great saving of labour can be made since the watering is carried out without opening the enclosures, since the covers 5 provide a right water feed or distribution. Moreover, the watering can be made at a right temperature, and when cultivations are in the open air, viz. when the enclosures are directly laid on the ground, the rain water is completely collected without losses. Moreover, a protection is provided against hail since these enclosures withstand perfectly important hail falls.

The enclosures are made of light materials and can therefore be quickly and easily transported when it is necessary to move them to another place.

In some cases, the enclosures described in FIGS. 1, 2 and 5 can be realized so as to be perfectly water tight and able to contain water for production of animals such as fish (fish breeding) decorative fish or fish for repopulating rivers. The covers forming a dish thus allow distributing feed in sufficient quantity and for a certain period of time by correctly adjusting the size or width of the holes or slits 7.

As hereabove described, the slits or holes 7 formed in the recessed surface 6 of the covers 5 having a general shape of discontinuous longitudinal cuts are generally identical in length and in alignment so as to confer to the cover 5 a maximum plate effect which is necessary for making the structure resistent. Moreover, in case where rain water is prohibited for a certain period of time or for particular species, it is possible to provide screens in the shape of plastics leaves with slightly folded back edges which fit into the covers 5 for forming umbrellas.

The herabove described enclosures enable collecting integrality of the sunshine, so that they can often be used as a substitute for large ambience standard greenhouse Thus is obtained on the one hand a reduction of capital investment and on the other hand an economy of energy. Finally, the rate of interventions on cultivations thus made is extremely limited and the task force much reduced.

What is claimed is:

1. An enclosure, comprising:
  at least one cover having edge means along the periphery of at least one central recessed substantially flat upper portion, said edge means having inner side walls facing the central flat portion, and outer side walls facing away from the central flat portion, said outer side walls being provided with holes, said recessed substantially flat portion including a plurality of calibrated and regularly spaced slits for admitting a penetration of liquid at a predetermined rate into the enclosure, and
  plugs having an axis and a diameter so as to sealably engage within each of said holes, each of said plugs being longitudinally translatably insertable in a respective one of said holes and including longitudinally extended radial slot means, said slot means communicating the interior of said enclosure with the exterior of the enclosure when the plug is pulled outwardly, along its axis, relative to the interior of said enclosure, each of said plugs and said cover cooperating to define means for admitting a quantity of air under said cover when the edge means of said cover are placed on a flat surface, said radial slot means in each of said plugs defining means for regulating the quantity of air admitted as each of said plugs is translated axially relative to its respective hole and means limiting the extension of said plug within the respective hole to prevent accidental removal of said plug in either direction along the axis of the plug.

2. An enclosure as set forth in claim 1, wherein said inner side walls include a graduated scale for measuring the quantity of liquid admitted by said slits in said central recessed portion.

3. The enclosures as set forth in claim 1, and further comprising at least one box having edges delimiting a flat area for said at least one cover, the edges of said box having upper portions formed with holes for removal of excess liquid from said box.

4. The enclosure as set forth in claim 3, and further comprising resilient fasteners for resiliently maintaining said at least one cover on said box.

5. The enclosure as set forth in claim 1, wherein at least one cover is placed directly on the ground with said ground delimiting a flat surface on which is placed said edge means of the cover, said edge means being driven into the ground and maintained by pegs to support the enclosure at different points around said edge means.

6. The enclosure as set forth in claim 1, wherein said at least one central recessed portion of said cover is provided with screens, said screens closing the slits for preventing a penetration of liquid through the cover.

7. The enclosure as set forth in claim 1, wherein said cover is made of a transparent, light and antirot material.

8. The enclosure as set forth in claim 1, wherein said cover is made of a translucent, light and antirot material.

9. The enclosure as set forth in claim 1, comprising at least two covers, each with at least one open end, with the open ends of two covers being placed adjacent one another.

10. The enclosure as set forth in claim 9, further comprising removable end pieces for closing the other ends of said covers.

11. The enclosure as set forth in claim 3, comprising at least two boxes, each with at least one open end, with the open ends of two boxes being placed adjacent one another, and crossbeams being further provided for transversely stiffening said boxes.

12. The enclosure as set forth in claim 3, wherein said box is bottomless.

13. The enclosure as set forth in claim 12 comprising at least one further lower box having edges on which is placed said bottomless box.

* * * * *

UNITED STATES PATENT AND TRADEMARK OFFICE
CERTIFICATE OF CORRECTION

PATENT NO. : 4,597,220
DATED : July 1, 1986
INVENTOR(S) : BOURRIE et al

It is certified that error appears in the above-identified patent and that said Letters Patent is hereby corrected as shown below:

Col. 2, line 33, after "plants", insert --to be--; and

Signed and Sealed this
Twenty-first Day of October, 1986

[SEAL]

*Attest:*

DONALD J. QUIGG

*Attesting Officer*      *Commissioner of Patents and Trademarks*

UNITED STATES PATENT AND TRADEMARK OFFICE
CERTIFICATE OF CORRECTION

PATENT NO. : 4,597,220
DATED : July 1, 1986
INVENTOR(S) : Bourrie et al

It is certified that error appears in the above-identified patent and that said Letters Patent is hereby corrected as shown below:

Column 2, line 37, "1 and 1" should read -- 2 and 3 --.

Signed and Sealed this

First Day of September, 1987

Attest:

DONALD J. QUIGG

Attesting Officer

Commissioner of Patents and Trademarks